Figure 1:
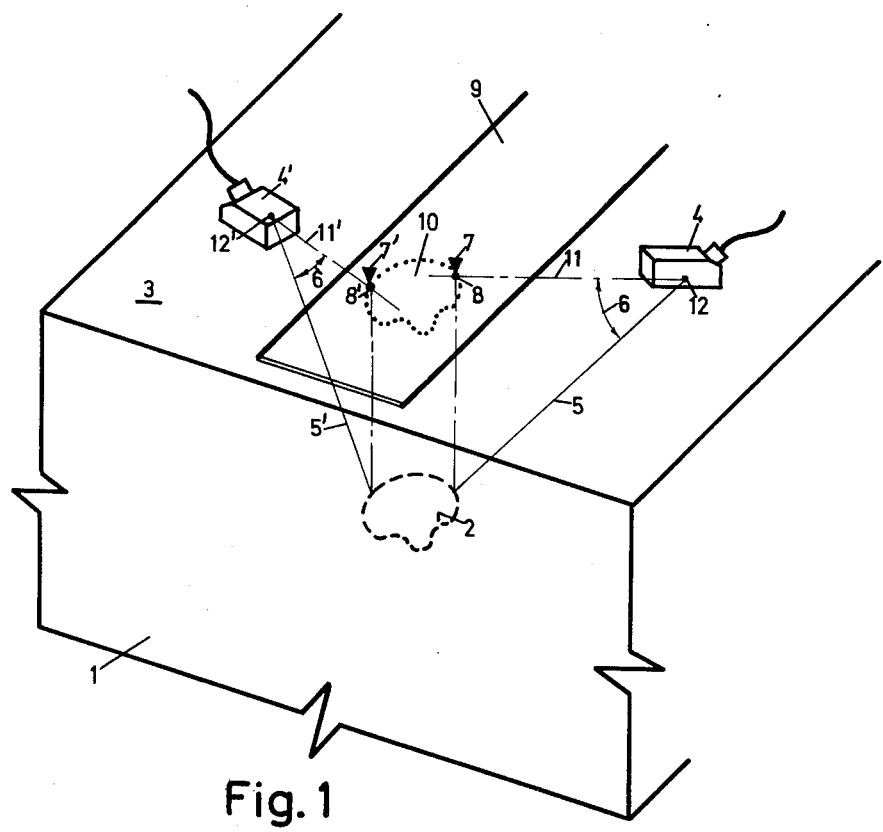

United States Patent [19]
Lund

[11] 3,962,909
[45] June 15, 1976

[54] METHOD AND APPARATUS FOR ULTRASONIC EXAMINATION

[75] Inventor: Svend Aage Lund, Birkerod, Denmark

[73] Assignee: Akademiet for De Tekniski Videnskaber, Svehsecentralen Glostrup, Denmark

[22] Filed: Sept. 3, 1974

[21] Appl. No.: 502,752

[30] Foreign Application Priority Data
Sept. 5, 1973 Denmark .......................... 4896/73

[52] U.S. Cl................................ 73/67.8 S; 73/67.9
[51] Int. Cl.². ......................................... G01N 29/04
[58] Field of Search............ 73/67.7, 67.8 R, 67.8 S, 73/67.9

[56] References Cited
UNITED STATES PATENTS
3,555,888   1/1971   Brown .............................. 73/67.8 S FOREIGN PATENTS OR APPLICATIONS
696,920   9/1953   United Kingdom................. 73/67.7

OTHER PUBLICATIONS
D. Sproule, An Ultrasonic Imaging System for Flaw Detection, Ultrasonics for Industry 1969, Conference Papers, London, England, Oct. 7–8, 1969.

*Primary Examiner*—Richard C. Queisser
*Assistant Examiner*—John P. Beauchamp
*Attorney, Agent, or Firm*—Schuyler, Birch, Swindler, McKie & Beckett

[57] ABSTRACT

It has previously been suggested to indicate, or record images of, internal inhomogeneities in a sample by means of an ultrasonic angle probe which is moved on the surface of the sample, the reflected echo signal being indicated as punctiform position markings in such a way that when added together the markings form an image of the projection of the inhomogeneities on the surface of the sample. It is now suggested that also the amplitudes of the echo signals are indicated, whereby much more information about the inhomogeneities is obtained. The amplitude can be indicated as a variation of the intensity, size and/or duration of the position markings. Another possibility is to indicate the amplitude by the length of a line segment.

27 Claims, 20 Drawing Figures

METHOD AND APPARATUS FOR ULTRASONIC EXAMINATION

Application Ser. No. 339,215 filed Mar. 8, 1973 relates to a method of indicating, or of recording images, of internal inhomogeneities in otherwise homogeneous bodies that have a substantially plane of slightly curved surface by ultrasonic examination according to the pulse-echo method, use being made of at least one angle probe which is guided across the surface of the body and scans its interior by emitting and receiving shortduration ultrasonic pulses in directions that form a predetermined angle differing from 90°, with the surface of the body, as well as by employing indicating means which, by being activated when reflected sound pulses are received, bring about punctiform markings on a substantially plane recording surface, which method is characteristic in that the markings on the recording surface are effected along a moving axis of indication which is guided in such a way in the plane of the recording surface that the displacement of a reference point on the axis of indication in relation to the recording surface follows the two-dimensional displacement of the sound emission point of the probe in relation to the surface of the body on a predetermined scale, and that the direction of the axis of indication in relation to the recording surface follows the direction of the projection of the sound path on the surface of the body, each marking being effected at a distance from the reference point that is proportional to the time interval which has elapsed from the emission to the reception of a sound pulse.

It is achieved hereby that the probe, as the examination proceeds, can be guided completely optionally across the surface of the body at different distances from and at different angles in relation to the occurring internal inhomogeneities continually emitting and receiving ultrasonic pulses while a geometrically correct marking of each and every reflected sound pulse in accordance with the location of the point of reflection in the interior of the body nevertheless takes place simultaneously in such a way that the markings are successively summed up into a coherent image of the projection on the surface of the body of all the internal inhomogeneities that are encountered by the sound beam and reflect this back to the probe.

The present invention relates to a method of the kind stated and aims at providing still more information about the reflecting inhomogeneities than has been possible to date.

In order that this may be achieved, the present invention is characterized in that on the recording surface, simultaneously with the production of each punctiform marking that indicates the presence and the position of a point of reflection in the interior of the examined body, a marking is produced which is dependent on the amplitude of the reflected sound pulse. Hereby a significant increase in the certainty and possible modes of application of the examination is achieved as compared to the prior art, and it is possible to simplify and reduce the cost of carrying out the examinations in practice. In addition to the indication, or direct recording of images, of the internal inhomogeneities, obtained according to said patent application, detailed information about the local structure, density and orientation of each individual point of reflection discovered is obtained by the present invention, something which has not been possible before with prior art ultrasonic examination methods.

According to the invention it is possible to effect the markings in such a way that the position marking and the amplitude marking corresponding to one and the same reflected sound pulse are coincident on the recording surface, the amplitude marking being produced by varying the intensity, size and/or duration of the position marking. Hereby a particularly simple method of producing the contemporaneous double marking of the position and structure of the internal points of reflection is obtained. It is possible according to the invention to produce markings with at least two predetermined fixed levels in accordance with the amplitude of the corresponding received, reflected sound pulse in such a way that echo pulses below a predetermined amplitude do not produce any marking, while more powerful echo pulses within predetermined amplitude intervals are each indicated by a fixed marking level associated with the amplitude interval in question. It is achieved hereby that insignificant interfering background noise can be suppressed while, at the same time, it is possible to lay down standardized limits for the marking so that, for instance, only points of reflection the reflection intensity of which exceeds an established level, produce a marking at a corresponding, established level of intensity.

An embodiment of the method according to the invention is characterized in that the electric echo signals generated by the individual reflected sound pulses received are passed through two amplifying circuits connected in parallel each with its own predetermined amplification factor, which two amplifying circuits are connected with the indication means in such a way that a marking is produced only when at least one of the amplifying circuits generates an output signal the amplitude of which exceeds a predetermined value, and in such a way that output signals the amplitude of which exceeds this value, produce markings having a predetermined first level of intensity if they come from the amplifying circuit which possesses the higher amplification factor, while they produce markings having a second predetermined level of intensity, by preference higher than the first, if they come from the amplifying circuit which possesses the lower amplification factor. It is achieved hereby that the examination as a whole can be carried out with a high level of sensitivity, that is to say, with a high amplification factor for the reflected signals, whereby insignificant points of reflection make themselves known by markings having a relatively low level of intensity, which may be taken as an indication of the fact that the apparatus operates normally, whereas reflected sound pulses from significant points of reflection produce markings having a substantially higher level of intensity and can, for this reason, be readily recognized as significant reflections that have to be examined more closely.

The disturbing effect which the marking of weak reflected sound pulses can have when examining markings originating from significant points of reflection can, according to the invention, be eliminated in that the reception of powerful echo pulses the amplitude of which exceeds a predetermined value and which consequently are indicated at a high marking level, automatically results in a simultaneous interruption of the marking of weaker echo pulses the amplitude of which lies below said predetermined value and which otherwise would be indicated at a low marking level.

Instead of allowing the position marking and the amplitude marking to be coincident as described in the foregoing, it is possible according to the invention to produce a series of punctiform markings as amplitude marking with collectively indicate a line segment which forms a predetermined angle to the axis of indication and the length of which increases monotonically with the amplitude of the reflected sound pulse. Since it is easier to read the length of a line segment than to read the intensity of a marking, this embodiment provides the possibility of a more positive ascertainment of the structure of the point of reflection than the embodiments mentioned in the foregoing, where it is the intensity of the marking which indicated the structure of the point of reflection.

According to the invention it is possible to indicate the line segment from one and the same point of reference which is fixed in relation to the axis of indication.

It is possible, however, for the line segment to be indicated at any time from the point on the axis of indication where a position marking is simultaneously produced. This facilitates the work of the operator in that it enables him to observe the position marking and the amplitude marking at the same time.

According to the invention it is possible to employ separate indicating means for the amplitude marking over and above those indicating means which are used for the position marking. Hereby the risk of the amplitude marking and the position marking coming to interfere with each other is reduced.

It is also possible, however, according to the invention to employ the same indicating means for the amplitude marking which are simultaneously used for the position marking. In this case the minimum number of indicating means can be employed.

In order to be able to distinguish with certainty the amplitude marking from the position marking, it is possible according to the invention to produce the punctiform markings which collectively constitute the amplitude marking with an intensity, size and/or duration which is different from and preferably less than the intensity, size and/or duration of the simultaneously produced corresponding position marking.

For the indication or for the permanent recording of the polar ultrasonic reflection characteristic of a point of reflection in the interior of the body it is possible, according to the invention, first to produce a position marking which indicates the presence and position of the point of reflection at its point of projection on the surface of the body, subsequent to which the probe is guided over the surface of the body in a circular movement around said point of projection as centre and with the axis of indication always passing through the point of projection.

In a corresponding manner it is possible, for the indication or permanent recording of the linear ultrasonic reflection characteristic of a point of reflection in the interior of the body, first to produce a position marking that indicates the presence and position of the point of reflection at its point of projection on the surface of the body with a selected direction of the projection of the sound path on the surface of the body, subsequent to which the probe is guided across the surface of the body in a parallel movement at right angles to the direction of the projection of the sound path on the surface of the body and to both sides of said point of projection.

These two last-mentioned embodiments of the method according to the invention are of very great importance for the provision of as much information as possible about an internal point of reflection and they make it possible to obtain a permanent documentation of the result of the examination, which is often so good that the structure of the point of reflection may be determined from the ultrasonic examination alone, possibly by comparison of the polar or linear ultrasonic reflection characteristics with standard sheets showing the appearance of the characteristics of the points of reflection occurring most frequently in practice.

The invention also relates to an apparatus for carrying out the method according to the invention, which apparatus is characteristic in-that the ultrasonic apparatus and the indicating means are adapted in such a way that on the recording surface, simultaneously with the production of each individual punctiform marking which indicates the presence and position of a point of reflection in the interior of the body examined, it is possible to provide a marking dependent on the amplitude of the reflected sound pulse.

The indicating means may according to the invention be substantially punctiform light diodes which each, in a manner known per se, via control circuits, is connected to the receiver part of the ultrasonic apparatus in such a way that the amplitude marking can be produced by varying the intensity and/or duration of the light emitted by the light diodes. The employment of light diodes provides the operator with the possibility of a direct visual recognition of reflected echo signals, and it is possible, by using photosensitive material, to obtain a permanent documentation of the result of the examination.

In those case where the apparatus, in addition to the indicating means that are employed for the position marking, also comprises separate indicating means for the amplitude marking, according to the invention a two-dimensional arrangement of indicating units may be utilized as indicating means which is designed and mounted in a manner known per se and which, via control circuits, is connected to the receiver part of the ultrasonic apparatus in such a way that it is possible to produce the position marking along the axis of indication at the same time as the amplitude marking can be produced as line segments which form a predetermined angle to the axis of indication and which at all times are indicated from the point on the axis of indication where a position marking is simultaneously produced. In this instance the advantage that the amplitude marking is separated from the position marking and thus does not interfere with the same, as well as the advantage that the amplitude marking and the associated position marking can easily be observed at the same time by the operator is achieved.

Finally, an embodiment of the apparatus according to the invention is characterized in that in addition to the angle probe and a holder with indicating units mounted on said probe, it consists only of a conventional emitting circuit and receiving circuit for electric pulses to and from the angle probe, as well as of a control circuit for activating the indicating units, which three circuits may expediently be assembled into a single integrated and preferably battery-powered unit. Hereby a portable miniature ultrasonic apparatus of pocket-size is obtained which the operator can easily carry on his person and which can be used under greatly varying circumstances, even in places where it can be difficult to make use of a normal ultrasonic apparatus. In addition, the apparatus will be very much cheaper than the prior art apparatuses which require the use of an oscilloscope including associated expensive control circuits.

The invention is explained below in greater detail with reference to the accompanying schematic drawings, in which FIG. 1 shows schematically and in perspective the principle of an ultrasonic examination according to the above mentioned patent application.

Figure 2A:
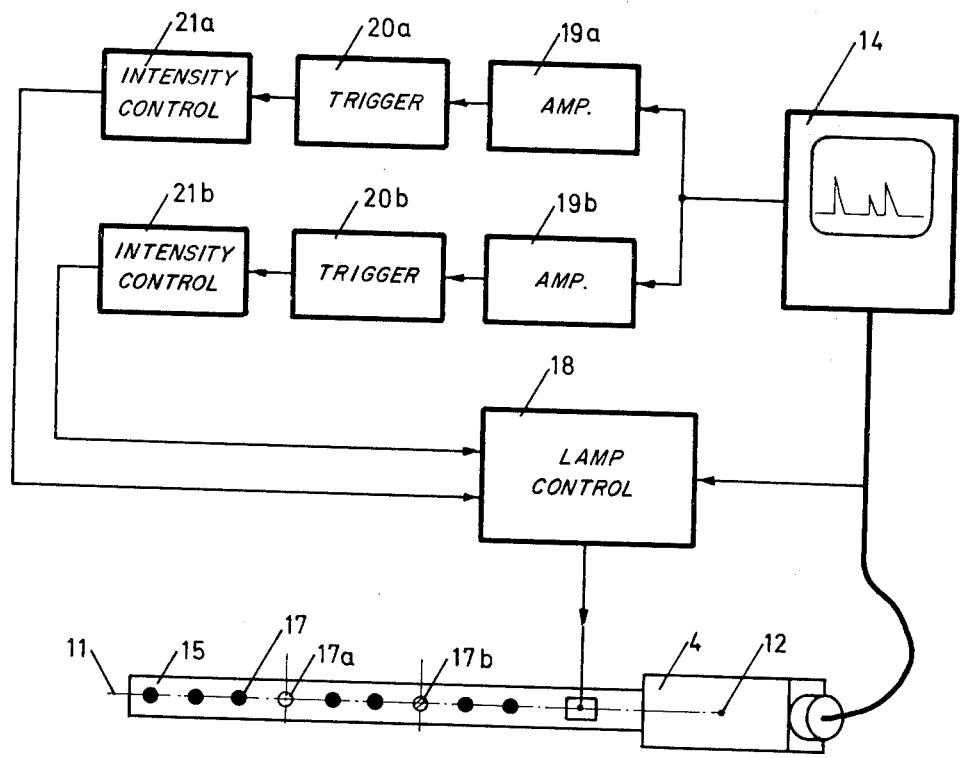
Figure 2B:
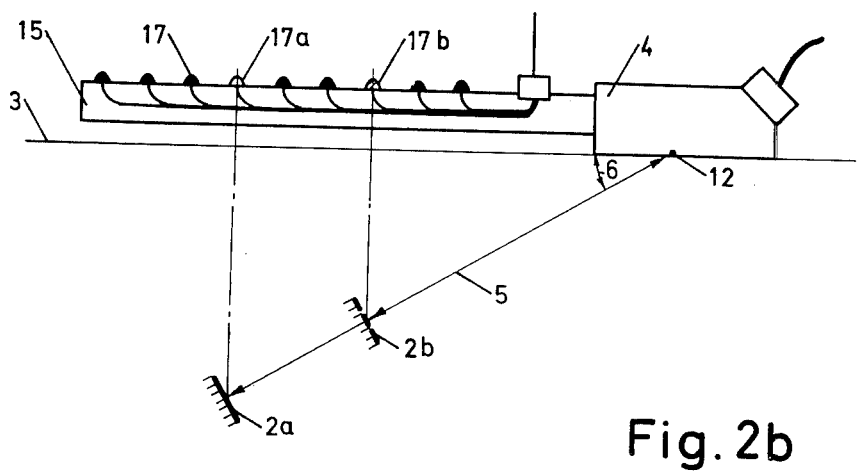
Figure 3:
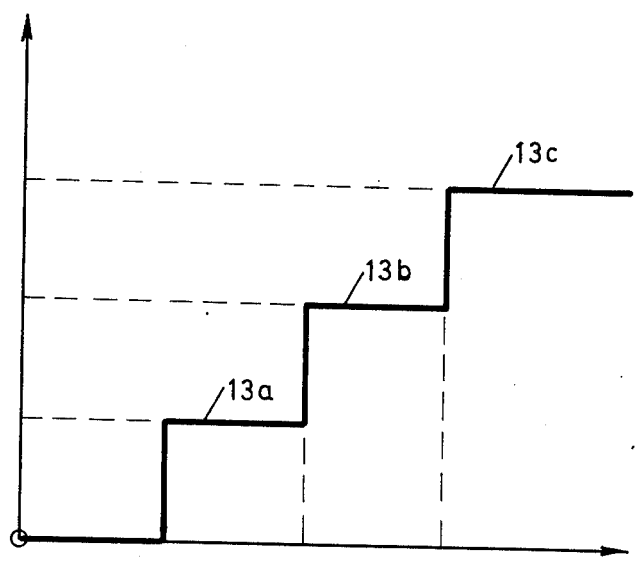
Figure 4A:
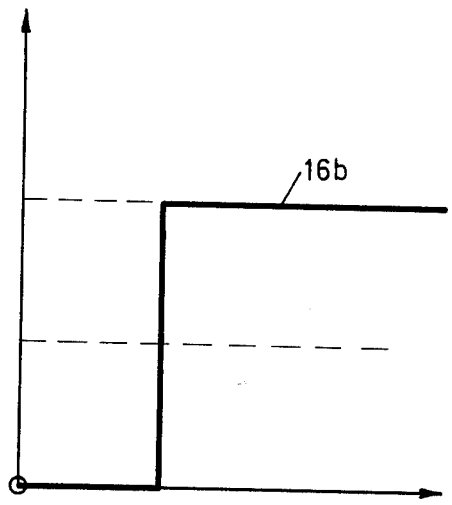
Figure 4B:
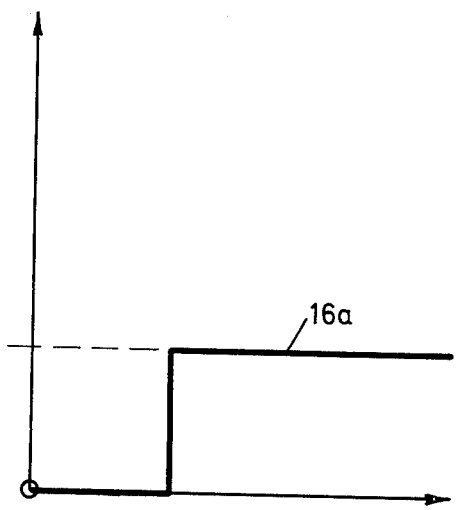
Figure 5A:
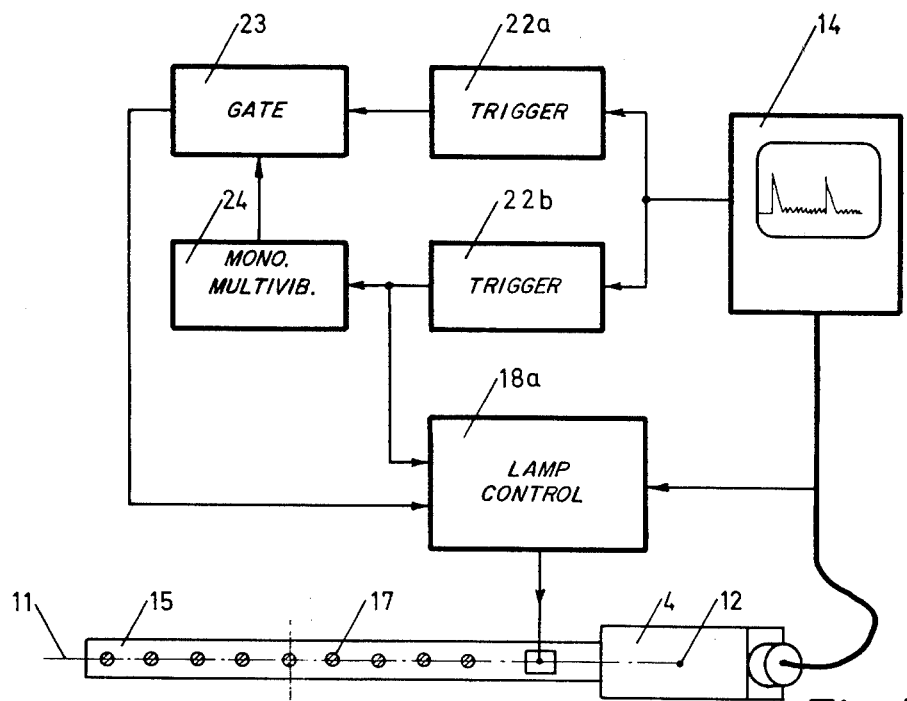
Figure 5B:
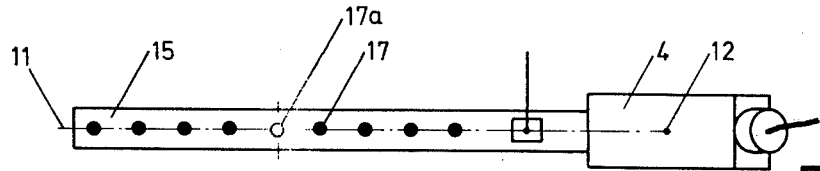
Figure 5C:
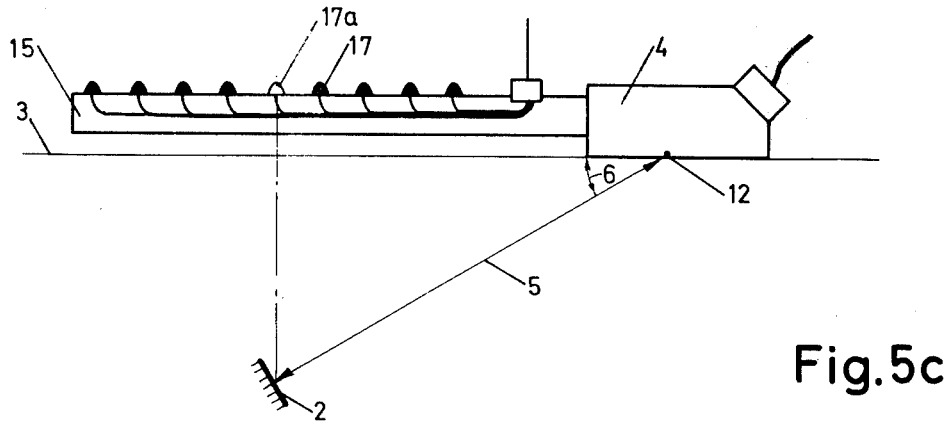
Figure 6A:
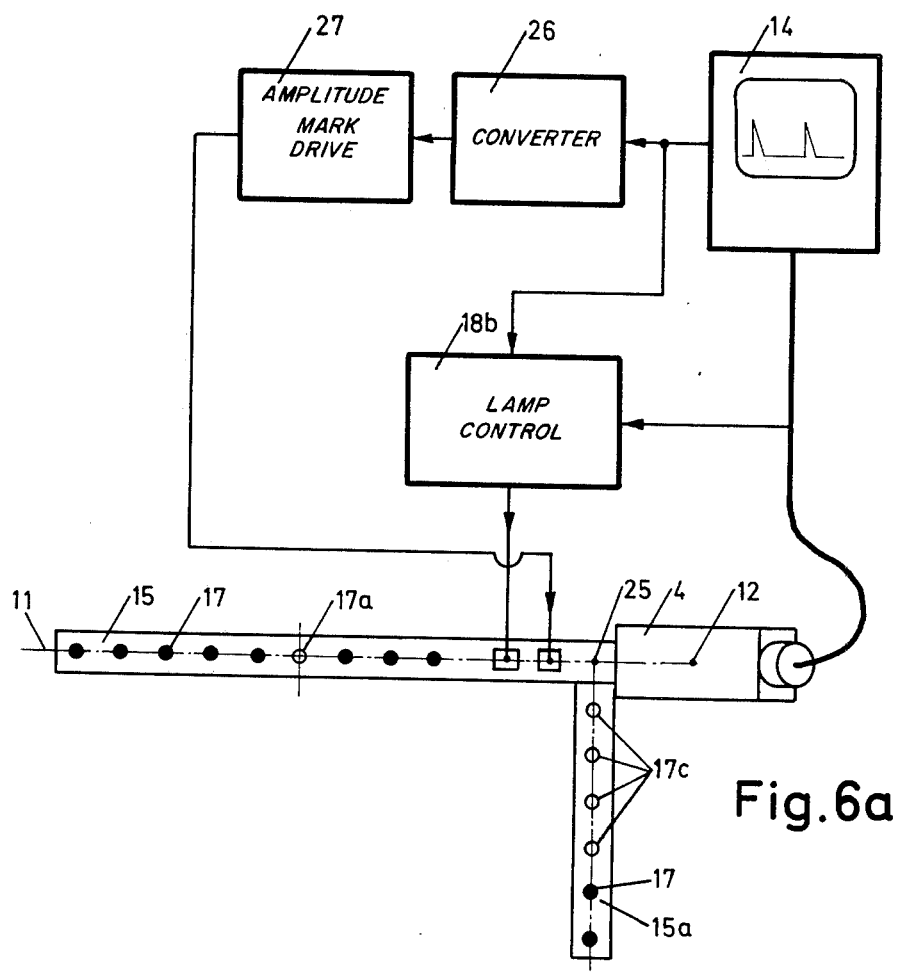
Figure 6B:
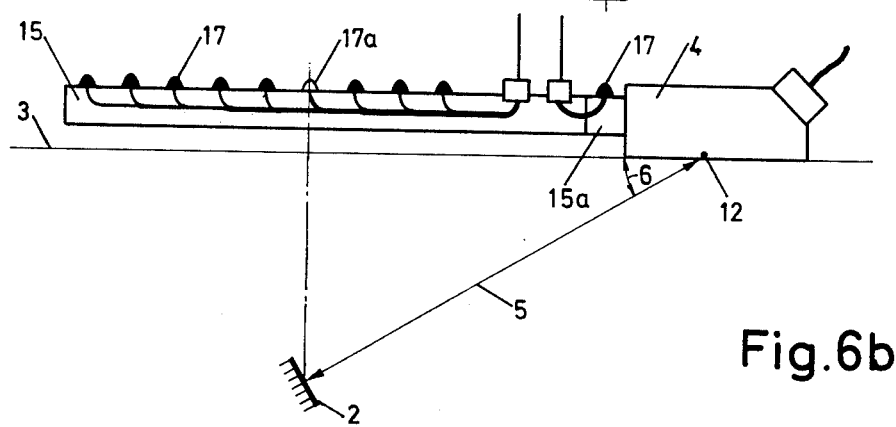
Figure 7A:
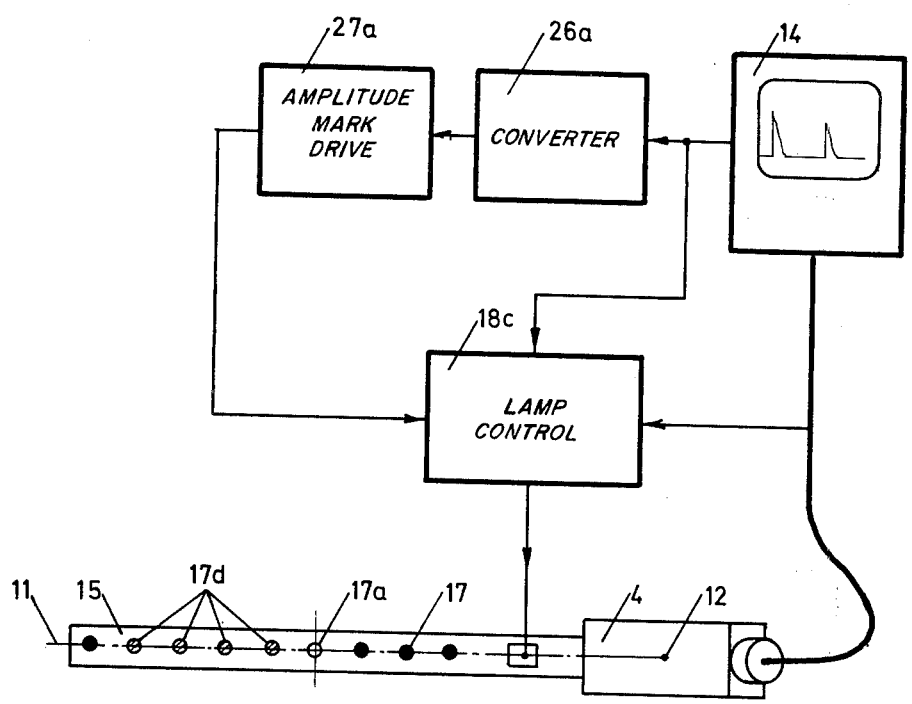
Figure 7B:
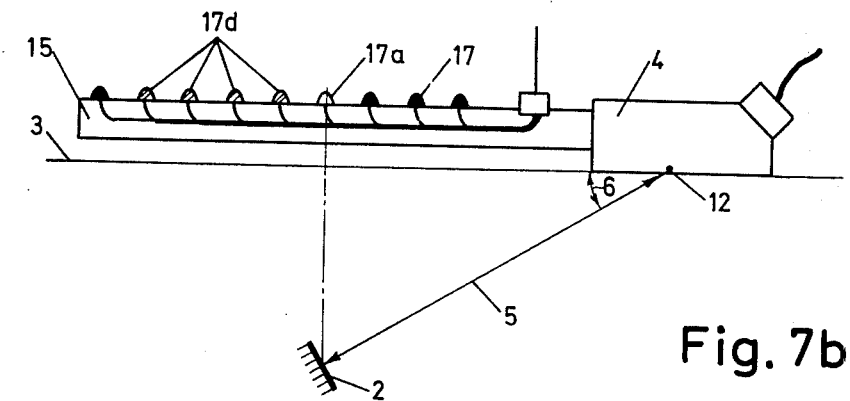
Figure 8A:
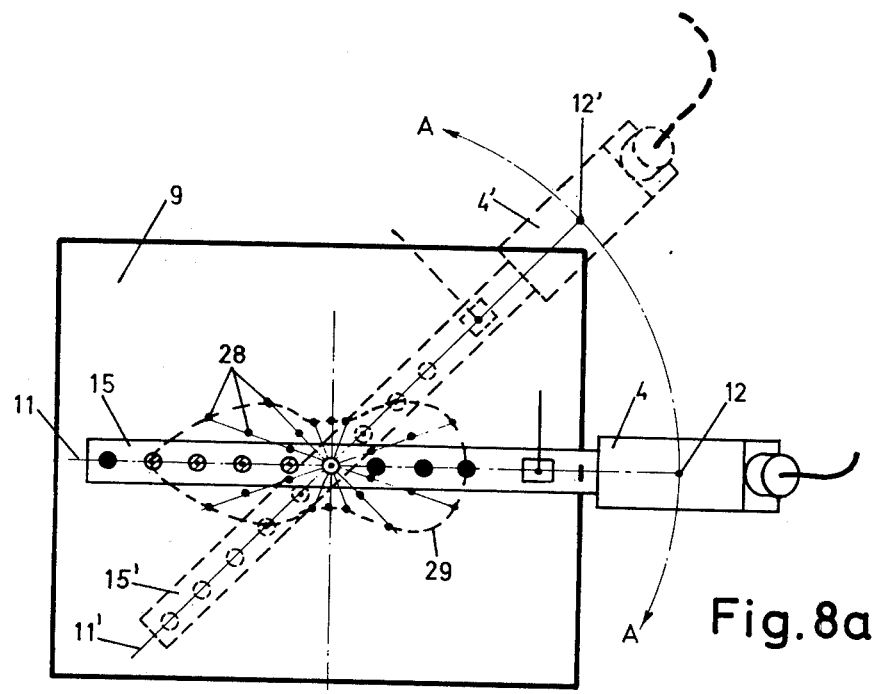
Figure 8B:
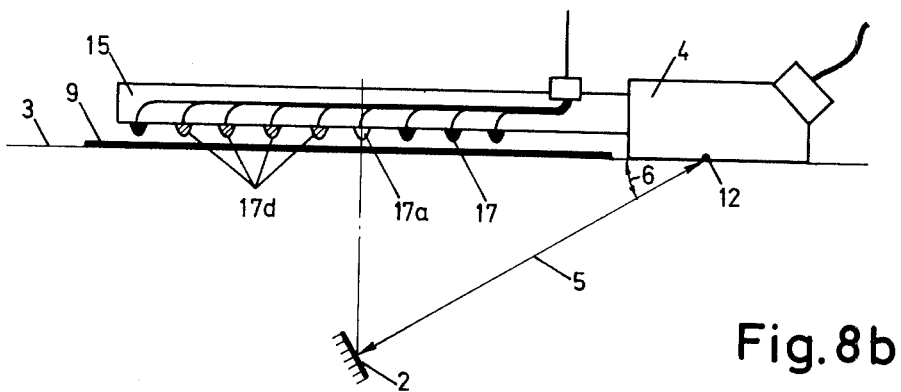
Figure 9A:
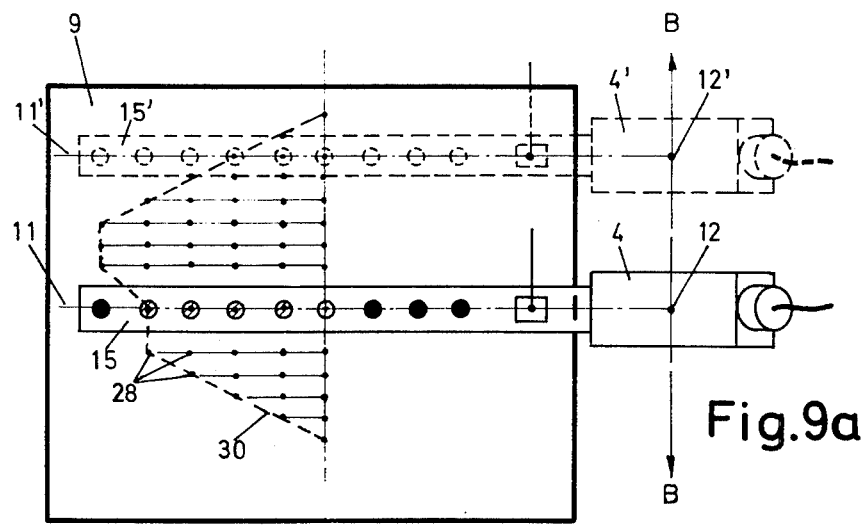
Figure 9B:
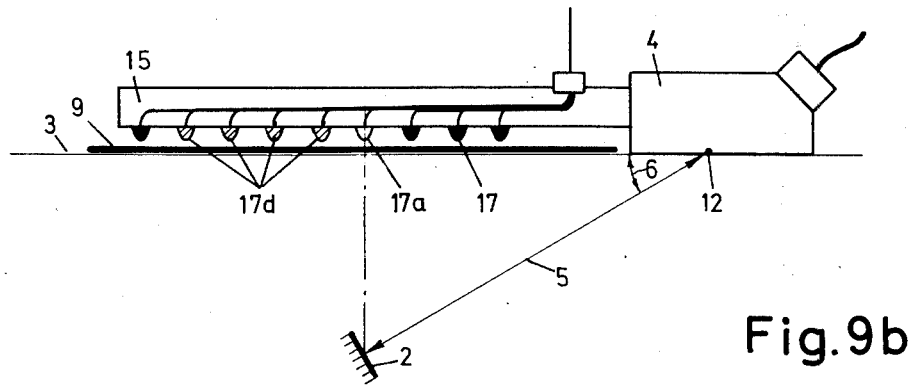
Figure 10A:
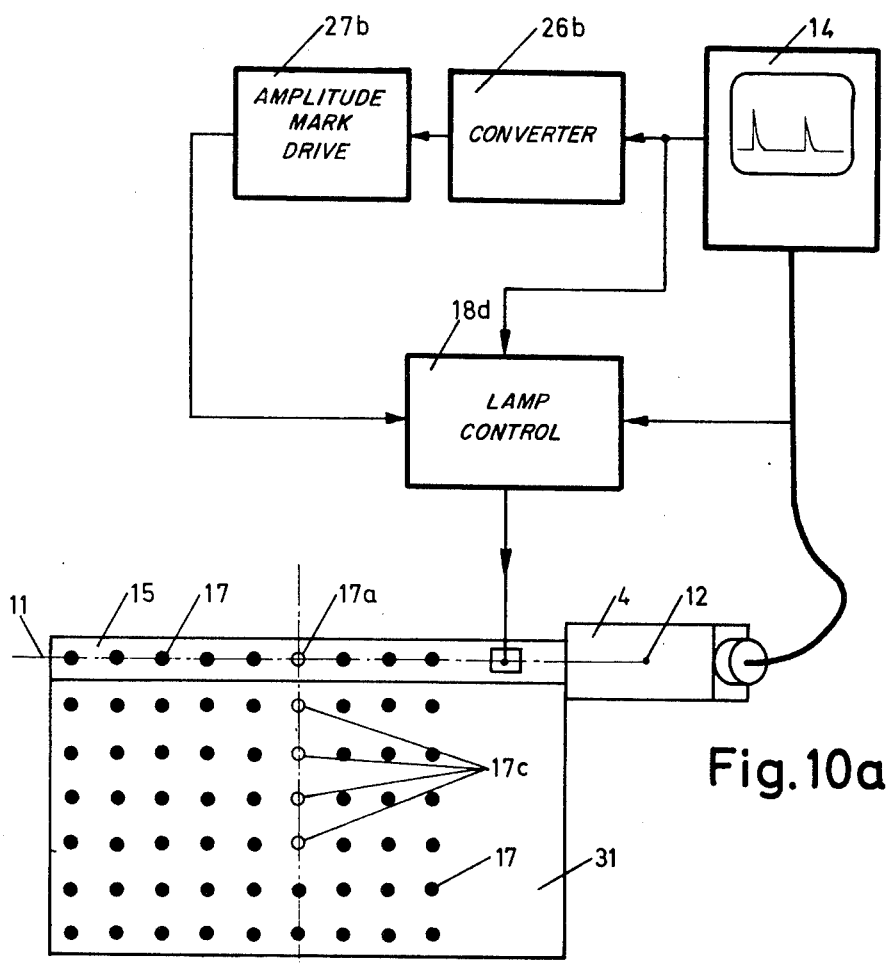
Figure 10B:
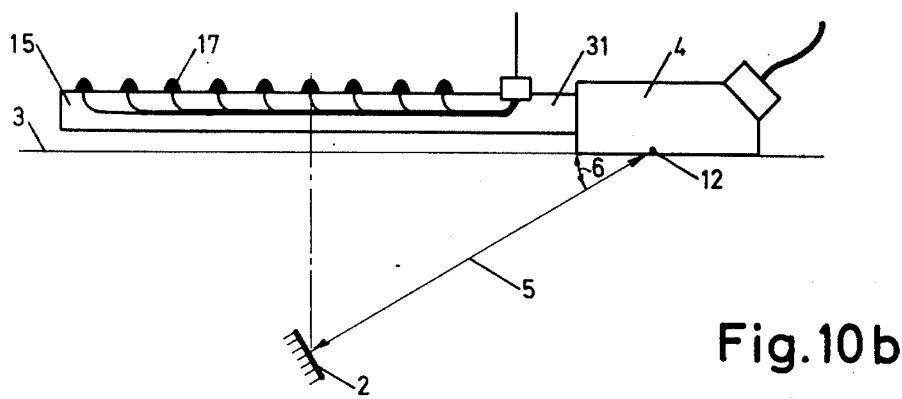
Figure 11:
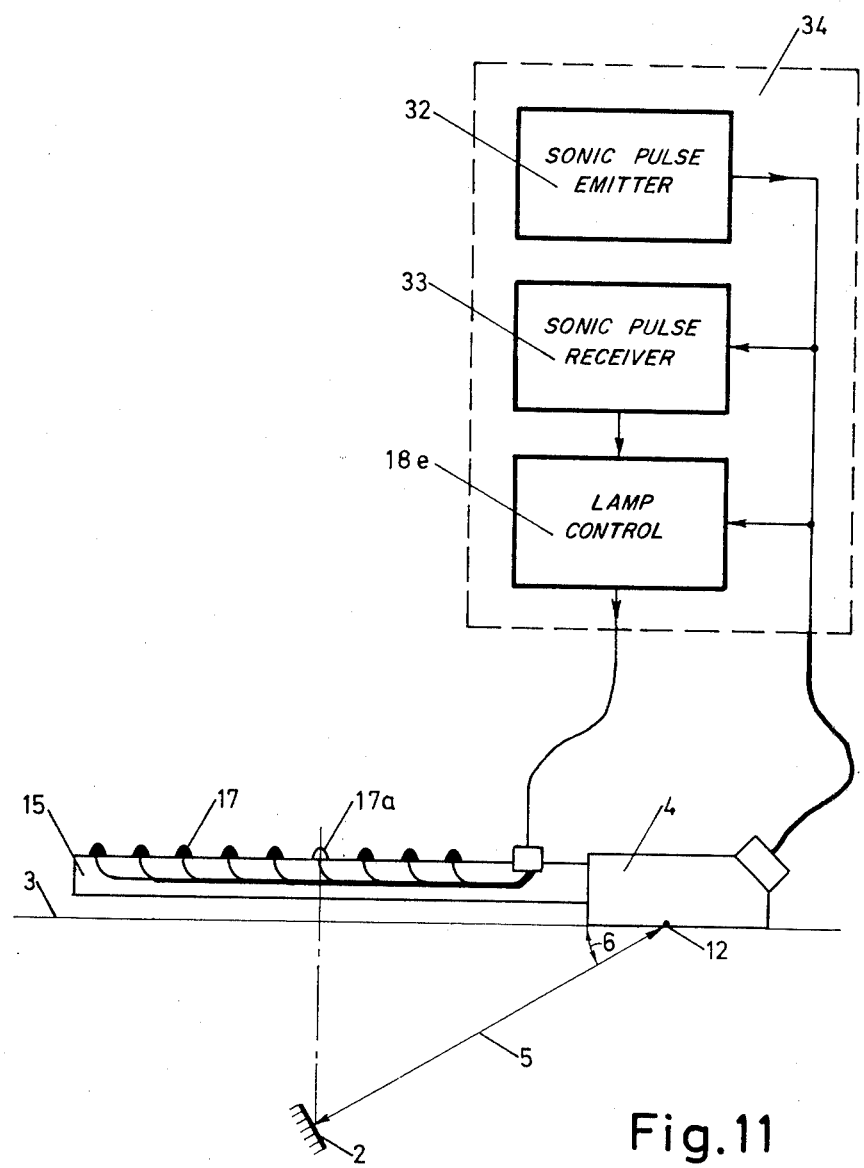

FIG. 2a shows schematically an embodiment of the apparatus according to the invention with the probe and the holder seen from above, FIG. 2b shows the probe shown in FIG. 2a with holder and indicating means seen from the side, FIGS. 3, 4a and 4b show diagrams for the explanation of the method according to the invention, FIG. 5a shows schematically a second embodiment of the apparatus according to the invention with ultrasonic probe, holder and indicating means seen from above, FIG. 5b shows the ultrasonic probe shown in FIG. 5a with holder and indicating units, likewise seen from above, but indicating another examination result, FIG. 5c shows the ultrasonic probe shown in FIG. 5b with holder and indicating means seen from the side, FIGS. 6a and 6b show a third embodiment of the apparatus according to the invention in the same form of illustration as in FIGS. 2a and 2b, FIGS. 7a and 7b show yet another embodiment of the apparatus according to the invention in the same form of illustration as in FIGS. 2a and 2b, FIG. 8a shows an ultrasonic probe with holder and indicating means seen from above and employed for recording a polar ultrasonic reflection characteristic, FIG. 8b shows the ultrasonic probe shown in FIG. 8a with holder and indicating means seen from the side, FIG. 9a shows an ultrasonic probe with holder and indicating means seen from above and employed for recording a linear ultrasonic reflection characteristic, FIG. 9b shows the ultrasonic probe shown in FIG. 9a with holder and indicating means seen from the side, FIGS. 10a and 10b show yet another embodiment of the apparatus according to the invention in the same form of illustration as in FIGS. 2a and 2b, and FIG. 11 shows an embodiment of a portable miniature ultrasonic apparatus in pocket-size with ultrasonic probe, holder and indicating means seen from the side.

In FIG. 1, a body is illustrated with an internal inhomogeneity 2 which acts as a point of reflection for ultrasonic pulses. These pulses are obtained with the aid of an ultrasonic probe 4 arranged on the plane or substantially plane surface 3 of the body, which probe is adapted to emit an ultrasonic beam 5 which forms an angle 6, differing from 90°, with the surface of the body. With the aid of indicating means 7 punctiform markings are produced on a recording material 9 which, in the present case, is placed on the surface 3 of the body. When the ultrasonic probe 4 is moved across the surface of the body in an appropriate manner, which is schematically indicated in FIG. 1 by showing the probe in a position 4', an image 10 of the internal inhomogeneity 2 will be plotted on the recording material 9. If the marking is effected along an axis of indication 11 which is fixed in relation to the ultrasonic probe 4 and is permanently parallel to the projection of the sound path 5 on the surface of the body, and if the marking is effected at a distance from the sound emission point 12 of the ultrasonic probe that is proportional to the time interval that has elapsed from the emission to the reception of an ultrasonic pulse with such a proportionality factor that the marking becomes the projection of the point of reflection, the image 10 formed will become a projection image of the internal inhomogeneity fully corresponding to the image that it would be possible to obtain by a radiographic process.

In the following it will be assumed that the axis of indication is always parallel to the projection of the ultrasonic path on the surface of the body and that the proportionality factor has such a value that the marking point is always the projection of the point of reflection on the surface of the body, but there is, however, nothing to prevent the axis of indication from having a direction entirely differing from the projection of the sound path on the surface of the body, if only it always follows this projection, and further the proportionality factor can be given a different value whereby, if this is desired, it is possible to obtain an enlargement or reduction of the image produced.

There is no need at all for the recording process to take place on or in the proximity of the surface of the body, if only the direction of the axis of indication always follows the direction of the projection of the sound path on the surface of the body, if the movement of a fixed reference point on the axis of indication follows the movement of the point of sound emission in relation to the surface of the body, and if the marking is effected at a distance from the reference point which is proportional to the time interval that elapses between the emission of a pulse and the reception of the associated echo.

The punctiform markings 8 can be produced in many different ways. By way of example, the employment of styli as indicating means 7 can be mentioned, which produce a blackening on the recording surface 9. A series of styli may be used mounted along the axis of indication 11 in a holder which is rigidly connected with the probe 4. It is also possible to employ a single stylus that is moved along the axis of indication. Another possibility is to utilize a facsimile registration technique with a helical projection on a cylinder which is made to rotate. It is also possible to let the result of the examination appear as luminous dots on the screen of a cathode ray tube. Furthermore, light sources, e.g. light diodes, may be used as indicating means, and in the embodiments described in the following precisely this form of indicating means has been employed. Normally, the light diodes are mounted in such a way on a holder that is rigidly connected to the ultrasonic probe that they are located on a line, the axis of indication, which is parallel to the reflection of the sound path on the surface of the body. The light diodes can be mounted on the topside of the holder and are then readily observable for the operator. If in this case a permanent recording of the result of the examination is desired, a stationary photographic camera with open shutter may be employed mounted above the area to be examined. The light diodes may also be mounted on the underside of the holder and it is then possible to produce a permanent recording by using a photosensitive material in the recording surface 9. It is possible, moreover, to mount indicating means both above and below the holder, e.g. light diodes above and styli underneath.

It has now been found possible in ultrasonic examinations of the kind dealt with to obtain significantly more valuable examination results, if the intensity of the reflected sound pulses is utilized, in addition to producing the punctiform marking which indicates the presence and position of a point of reflection, for producing a marking dependent of the amplitude on the reflected sound pulse.

An example of an apparatus which makes it possible to produce such an amplitude-dependent marking is shown in FIGS. 2a and 2b. On the ultrasonic probe 4 a holder 15 is mounted which, on its topside, carries a line of light diodes 17, all of which are located on the axis of indication 11.

In FIGS. 2a and 2b as well as in the following figures, a switched-off light diode is indicated by a filled-in symbol 17, a faintly luminous light diode by a hatched symbol 17b and 17d, and a strongly luminous light diode by a not-filled-in symbol 17a and 17c.

In FIG. 2a, the ultrasonic probe 4 is shown connected with a conventional ultrasonic apparatus 14 for the generation of ultrasonic pulses that are emitted from the sound emission point 12 of the ultrasonic probe in direction 5 and which, in the example illustrated, encounter two points of reflection, that is to say, a point of reflection 2b giving a faint echo, and a point of reflection 2a giving a strong echo. The echo signals received by the ultrasonic probe are supplied to the ultrasonic apparatus 14 and are displayed on the screen of the cathode ray tube together with the ultrasonic pulse emitted. The electric signals which correspond to the emitted ultrasonic pulse and the received echo pulses, are also supplied to an electronic control circuit 18, which controls the light diodes in such a way that it causes the light diodes 17a and 17b, which are located directly above the projection of the points of reflection on the surface 3 of the body, to become luminous.

The intensity with which the diodes are luminous depends on the magnitude of the associated echo, and this dependence is brought about with the aid of two lines of electronic-circuits that are controlled by the ultrasonic apparatus 14. One line comprises an amplifier 19a with high amplification followed by a trigger 20a which triggers when the signal from amplifier 19a exceeds a predetermined level and thereby has the effect that an intensity control circuit 21a via the electronic control circuit 18 causes the diode in question 17b to become luminous at a relatively low intensity 16a, cf. FIG. 4b. Another line comprises an amplifier 19b with low amplification followed by a trigger 20b, which is identical with trigger 20a, followed by an intensity control circuit 21b which, via the electronic control circuit 18, causes the diode in question 17a to become luminous at a high intensity 16b, cf. FIG. 4a.

As long as the amplitude of the received echo signals is so low that the output signal even from the amplifier 19a with high amplification is insufficient for triggering the associated trigger 20a, the electronic control circuit 18 has the effect that the diodes in question are not switched on. If the echo signal has such an amplitude that the output signal from amplifier 19a is capable of triggering trigger 20a, while the output signal from amplifier 19b, which has a lower amplification, is not capable of triggering trigger 20b, the diode in question will become luminous at a low intensity 16a. This is the situation of the point of reflection 2b in FIG. 2b. The echo signal from this point of reflection thus has the effect that diode 17b becomes luminous at a low intensity. If, finally, the amplitude of the echo signal is so high that also the output signal from amplifier 19b is capable of triggering trigger 20b, the diode in question will then become luminous at a high intensity 16b. This is the situation of the point of reflection 2a in FIG. 2b. The echo signal in this case has the effect that the associated diode 17a becomes luminous at a high intensity.

In FIGS. 2a and 2b it is shown how it is possible to obtain two different levels of intensity 16a and 16b for the light of the diodes, cf. FIGS. 4a and 4b.

In FIG. 3, the possibility of obtaining several different levels of marking intensity 13a, 13b and 13c in dependence of a corresponding number of amplitude intervals for the echo signals is shown in a more general manner.

In FIGS. 5a, 5b and 5c, an apparatus is illustrated which makes it possible, as long as the ultrasonic beam does not impinge upon a significant reflecting inhomogeneity, to obtain a faint light from all the light diodes for providing an indication that the apparatus is operative and that ultrasonic contact exists with the body, whereas when the ultrasonic beam impinges upon a significant point of reflection, a powerful light is obtained from the diode in question while the other diodes are switched off.

In FIGS. 5a, 5b and 5c, as well as in the following figures, elements that correspond to elements shown in FIGS. 2a and 2b, are indicated with the same reference designations and are not explained in greater detail.

In FIG. 5a it is shown how a signal from the ultrasonic apparatus 14 is supplied, on the one hand, to a trigger 22a having a low triggering level and, on the other hand, to a trigger 22b having a high triggering level. The output signal from trigger 22a is supplied through a gate circuit 23 to the electronic control circuit 18a, where it has the effect that even very weak signals cause the light diodes 17 to become luminous at a low intensity. If the ultrasonic beam 5 impinges upon a point of reflection 2 which gives an echo with a significant amplitude, trigger 22b is also triggered, which has the effect that a monostable multivibrator 24 is switched over and thereby closes gate circuit 23. At the same time, the output signal from trigger 22b is supplied to the electronic control circuit 18a, whereby it is achieved that the light diode in question 17a shines with great intensity. As gate circuit 23 is closed, the other diodes 17 are switched off. This situation is shown in FIGS. 5b and 5c.

In the embodiments described with reference to FIGS. 2a, 2b, 5a, 5b and 5c, the same light diodes are employed for indicating the presence and position of a point of reflection and for producing a marking dependent of the amplitude of the echo signal. In FIGS. 6a and 6b, an apparatus is shown where separate light diodes that are different from the position light diodes are employed for indicating the amplitude.

The apparatus illustrated comprises, besides the holder 15, a holder 15a which is perpendicular thereto and likewise rigidly connected with the ultrasonic probe 4, and which carries a line of light diodes 17. From the ultrasonic apparatus 14, a signal is supplied to the electronic control circuit 18b which has the effect that, when an echo pulse is received from a point of reflection 2, a light will be produced in the proper light diode 17a mounted in holder 15 for indicating the position of the point of reflection. The signal from the ultrasonic apparatus 14 is also supplied to a voltage to number converter 26, the output signal of which has via an amplitude marking drive step 27 the effect that a number of the diodes mounted in holder 15a become luminous. This number is proportional to the amplitude of the echo signal and the diodes 17c in question collectively indicate a luminous line segment, the length of which is a measurement of the amplitude of the echo signal. The line segment is indicated from a fixed reference point 25 on the axis of indication 11.

In FIGS. 7a and 7b, an apparatus is illustrated in which the amplitude marking, as in FIGS. 6a and 6b, is effected by means of light diodes which indicate a line segment, the length of which is proportional to the amplitude of the echo pulse, however, as distinct from the apparatus illustrated in FIGS. 6a and 6b, the amplitude marking is here effected from a variable point, that is to say, from the point which indicates the position of the point of reflection, and the same diodes are utilized for both the position marking and the amplitude marking. In order to be able to distinguish the amplitude marking 17d from the position marking 17a, the former marking is effected with a lower intensity of light than the latter marking. The apparatus shown in FIG. 7a comprises, as the apparatus illustrated in FIG. 6a, a voltage to number converter 26a and an amplitude marking drive step 27a, as well as an electronic control circuit 18c adapted to the special mode of operation.

It will be seen that diode 17a, which corresponds to the position of the point of reflection 2, shines with a high intensity, whereas the light diodes 17d, whose number depends of the amplitude of the echo signal, shine with a lower intensity.

In FIGS. 8a and 8b it is shown how, with the aid of the apparatus illustrated in FIGS. 7a and 7b, it is possible to record a complete polar ultrasonic reflection characteristic of the point of reflection in question.

Subsequent to the detection of the point of reflection 2, the ultrasonic probe and the holder are pivoted around the position-marking light diode 17a so that the axis of indication 11 always passes through the point of projection of the point of reflection, whereby the sound emission point 12 of the ultrasonic probe describes a circular arc A—A. Subsequent to a rotation of 360°, the punctiform amplitude markings 28 will collectively form a surface, the limiting curve of which constitutes the polar ultrasonic reflection characteristic 29. In FIGS. 8a and 8b, the light diodes are mounted on the underside of the holder so that they are able to illuminate a photosensitive registration surface 9.

In FIGS. 9a and 9b, it is illustrated in a corresponding manner how, with the aid of the apparatus shown in FIGS. 7a and 7b, it is possible to obtain a linear ultrasonic reflection characteristic. Subsequent to the detection of a point of reflection 2, the ultrasonic probe 4 with holder 15 are moved in a translatory movement at right angles to the axis of indication 11 so that the point of ultrasonic emission 12 follows the straight line B—B. In this case, amplitude markings 28 will collectively form a surface, the limiting curve of which constitutes the linear ultrasonic reflection characteristic 30 of the point of reflection in question.

The polar and the linear ultrasonic reflection characteristics provide very important information about the structure of the point of reflection, and it is possible to draw standard diagrams of the reflection characteristics of most inhomogeneities occurring in practice, so that by means of a simple comparison between the recorded ultrasonic reflection characteristics and the standard diagrams it is possible, in a very simple manner, to obtain significant information about the point of reflection in question.

In FIGS. 10a and 10b, an apparatus is illustrated in which, to the holder 15 for the light diodes for position marking, a holder 31 is attached containing a two-dimensional arrangement of light diodes for amplitude marking. The apparatus, the design of which corresponds substantially to the design of the apparatuses shown in FIGS. 6a and 7a, brings about a control of the diodes in holder 31 of such a kind that the luminous diodes 17c collectively form a line segment, the length of which depends of the amplitude of the echo pulse, extending at right angles from the axis of indication 11 and on a level with the light diode 17a which indicates the position of the point of reflection. This embodiment possesses the advantage that the position marking is separated from the amplitude marking in such a way that these markings do not interfere with each other, while, at the same time, these two markings are effected in the immediate proximity of each other so that it is easy to observe them simultaneously. If it is desired, the amplitude marking may be effected with an intensity that is different from that of the position marking.

FIG. 11 illustrates an ultrasonic apparatus that is constructed as a miniature apparatus in pocket-size. In addition to the ultrasonic probe 4 with the associated holder 15 and light diodes 17, the apparatus comprises only an emitter 32 for ultrasonic pulses, a receiver 33 for the echo pulses and an electronic control circuit 18e. Component parts 32, 33 and 18e are expediently assembled into one apparatus 34 which may be powered by a battery. The apparatus 34 can easily be manufactured in such a small size that it may readily be carried in a pocket, and since the apparatus can be independent of extraneous current supply, it can be employed for examinations under almost all circumstances. Moreover, it is possible for the apparatus to be produced at a significantly lower price than the prior art ultrasonic apparatuses which comprise an oscilloscope and associated, expensive control circuits. This has been made possible by the fact that the information about the amplitude of the reflected sonic pulse, which in prior art apparatuses is obtained from the oscilloscope, is here marked on the registration surface together with the position marking. If so desired, the apparatus 34 may be assembled together with the ultrasonic probe 4 in such a way that the entire ultrasonic examination apparatus consists of one single unit. The apparatus illustrated in FIG. 11 can be designed as indicated in one or several of the preceding figures.

In the embodiments described above light diodes are employed as indicating means. However, the invention is not restricted hereto, but can also be applied in connexion with other indicating means, such as styli or the screen of a cathode ray tube.

In the embodiments described the amplitude is indicated by the intensity of the luminosity of the light diodes or by the length of a line segment which is defined by a line of luminous diodes. It is also possible, however, to indicate the amplitude in other ways, e.g. by the blackening or by the size of the punctiform markings produced by a stylus, or by the duration of the luminous periods of an intermittent light source.

What is claimed is:
1. A method of indicating, or of recording images of internal inhomogeneities in otherwise homogeneous bodies which have a substantially plane or slightly curved surface by ultrasonic examination according to the pulse echo method, including guiding at least one angle probe connected to an ultrasonic apparatus across the surface of the body to scan its interior by emitting and receiving short-duration ultrasonic pulses in directions that form a predetermined angle with the surface of the body, and activating indicating means in response to received reflected sound pulses to produce punctiform markings on a substantially plane recording surface, characterized by the steps of moving the indicating means having an axis of indication along which the markings on the recording surface are made to thereby move the axis in the plane of the recording surface in such a way that the displacement of a reference point on the axis of indication in relation to the recording surface follows the two-dimensional displacement of the sound emission point of the probe in relation to the surface of the body on a predetermined scale, the axis of indication in relation to the recording surface following the direction of the projection of the sound path on the surface of the body, each of said markings being effected at a distance from the reference point that is proportional to the time interval that has elapsed from the emission to the reception of a sound pulse, detecting the amplitude of each of said returned sound pulses, and simultaneously with each of said distance proportional markings being effected, producing a marking having a characteristic subject to a variable modulation as a function of the amplitude of each of said reflected sound pulses whereby the intensity of the reflected sound pulse is recorded in the image of said inhomogeneity.

2. A method as claimed in claim 1, wherein the position marking and the amplitude marking corresponding to one and the same reflected sound pulse are coincident on the recording surface, the amplitude marking being produced by varying the intensity or size of the position marking.

3. A method as claimed in claim 2, including the steps of establishing different amplitude levels at which means for making said amplitude markings will operate, comparing each of said reflected sound pulses to said amplitude levels so that said pulses below said predetermined amplitude levels do not produce any marking, pulses of greater than a first predetermined amplitude level of said two levels are indicated by a first fixed marking indication of said marking means and pulses of greater than a second amplitude level of said levels are indicated by a second fixed marking indication of said marking means.

4. A method as claimed in claim 3, wherein said comparing step comprises supplying said received, reflected sound pulses to two parallel-connected amplifying circuits each with a different amplification factor, said two amplifying circiuts being connected with the indicating marking means, and said indicating step comprises producing markings at least at a predetermined first intensity level if the marking indication comes from the amplifying circuit which has the higher amplification factor, while producing markings at least at a predetermined second intensity level higher than the first intensity level, if the marking indication comes from the amplifying circuit that has the lower amplification factor.

5. A method as claimed in claim 4, wherein an output from said amplifying circuit having the lower amplification level and thereby indicating a strong reflected sound pulse interrupts the output of said amplifying circuit having a higher amplification level.

6. A method as claimed in claim 1, wherein each of said amplitude markings is formed by defining a line segment at a predetermined angle to the axis of indication, the length of said line segment monotonically increasing with the amplitude of the reflected sound pulse.

7. A method as claimed in claim 6, wherein each of said line segments have as their point of origin the same reference point which is fixed in relation to said axis of indication.

8. A method as claimed in claim 6, wherein each of said line segments have as their point of origin the corresponding point on the axis of indication where a position marking is simultaneously produced.

9. A method as claimed in claim 6, wherein said amplitude markings are produced with an intensity or size and/or duration which is different from the intensity or size of the simultaneously produced corresponding position marking.

10. A method as claimed in claim 7, wherein said amplitude markings are produced with an intensity or size which is different from the intensity or size of the simultaneously produced corresponding position marking.

11. A method as claimed in claim 9, for recording the polar ultrasonic reflection characteristic of one of said points of reflection of said inhomogenity in the interior of the body, wherein first said position marking which indicates the presence and the position of the points of reflection is produced at its point of projection on the surface of the body, subsequent to which the probe is guided over the surface of the body in a circular movement using said first point of projection as center of the circle and with the axis of indication always passing through said first point of projection.

12. A method as claimed in claim 7 for recording the linear ultrasonic reflection characteristic of one of said points of reflection of said inhomogeneity in the interior of the body comprising first establishing a position marking, which indicates the presence and the position of a point of reflection of an inhomogeneity at its point of projection on the surface of the body, and guiding the probe across the surface of the body in a movement at right angles to the direction of the projection of the sound path which produced said point of projection, the probe remaining parallel to said axis of indication, the movement being on the surface of the body and to both sides of said point of projection.

13. An apparatus for indicating, or for recording images of internal inhomogeneities in otherwise homogeneous bodies which have a substantially plane or slightly curved surface by ultrasonic examination according to the pulse echo method, comprising an ultrasonic apparatus having at least one angle probe connected thereto and indicating means responsive to said ultrasonic apparatus which, by being activated when reflected sound pulses are received by said ultrasonic apparatus produce punctiform markings on a substantially plane recording surface, characterized by means to move the indicating means having an axis of indication along which the markings on the recording surface are made to thereby move this axis in the plane of the recording surface so that the displacement of a reference point on the axis of indication in relation to the recording surface follows the two-dimensional displacement of the sound emission point of the probe in relation to the surface of the body on a predetermined scale, the direction of the axis of indication in relation to the recording surface following the direction of the projection of the sound path on the surface of the body, the indicating means producing markings at a distance from the reference point that is proportional to the time interval that has elasped from the emission of a sound pulse to the reception of a reflected sound pulse from said inhomogeneity, said indicating means further including means for detecting the amplitude of each of said returned sound pulses and simultaneously with each of said distance proportional markings being effected, producing a marking having a characteristic of the markings subject to a variable modulation in dependence on the amplitude of the received reflected said pulse, whereby the intensity of the reflected sound pulse is recorded in the image of said inhomogeneity.

14. An apparatus as claimed in claim 13 wherein the means for producing the position marking and the means for producing the amplitude marking produce marks corresponding to the same reflected sound pulse coincidently on the recording surface, said means for producing the amplitude marking modulating the intensity or size of the position marking.

15. An apparatus as claimed in claim 14 wherein the indicating means comprise substantially punctiform light diodes, each individual one of said light diode being connected to a receiver portion of the ultrasonic apparatus and responsive to the output of the receiver portion to produce the amplitude marking by modulating the intensity or of the light emitted by the light diodes.

16. An apparatus as claimed in claim 14 wherein said amplitude indicating means includes means for fixing first and second amplitude levels for responding to said reflected sound pulses, said amplitude indicating means being unresponsive to signals below the first and second amplitude level, providing a first response to signals in excess of said first amplitude level and a second response to signals in excess of said second amplitude level.

17. An apparatus as claimed in claim 16 wherein said amplitude indicating means receive the echo signals generated by the individual received, reflected sound pulses and includes first and second amplifying circuits connected in parallel each with its own predetermined amplification factor, said two amplifying circuits being connected with the indicating means output and including said means for fixing said first and second amplitude levels, the output of said first amplifying circuit providing one of said amplitude indicating marks at a predetermined first intensity level, said second amplifying circuit having a higher amplification factor than said first amplifying circuit and producing intensity markings at a second lower intensity level than said first amplifying circuit.

18. An apparatus as claimed in claim 17 and including switching means coupled between said first and second amplifying circuits and responsive to an output signal from said first amplifying circuit to preclude a marking indication from said second amplifying circuit.

19. An apparatus as claimed in claim 13, wherein the indicating means for the amplitude marking comprise means for producing the amplitude marking in the form of a series of punctiform markings which collectively establish a line segment at a predetermined angle to the axis of indication, the length of said line segment monotonically increasing with the amplitude of the reflected sound pulse.

20. An apparatus as claimed in claim 19, comprising means for mounting the indicating means for establishing said line segments at a fixed point of reference in relation to the axis of indication.

21. An apparatus as claimed in claim 19 comprising means for mounting the indicating means for establishing each of said line segments with a point of origin at the point on the axis of indication where the corresponding one of the position markings is simultaneously produced.

22. An apparatus as claimed in claim 19 wherein separate elements are provided for establishing the position marking and the amplitude marking.

23. An apparatus as claimed in claim 13 characterized in that the indicating means which are employed for the position marking can simultaneously be employed for the amplitude marking.

24. An apparatus as claimed in claim 22 wherein said means for producing the amplitude marking for each reflected sound pulse produces said amplitude marking with an intensity or size which is different from the intensity or size and/or duration of the corresponding position marking of each said reflected sound pulse simultaneously produced by said distance indicating means.

25. An apparatus as claimed in claim 22 wherein said elements for establishing the position and amplitude markings comprise punctiform light diodes connected to the ultrasonic apparatus, and responsive to the reflected pulses received thereby, the light diodes being activated to appear as a more or less strongly luminous dot.

26. An apparatus as claimed in claim 22 wherein the indicating means comprise a two-dimensional array of indicating units, said array being connected to the ultrasonic apparatus and responsive to the reflected pulses received thereby to energize one of said units to produce the position marking along the axis of indication and to energize one or more of said units simultaneously to establish the amplitude marking as the line segment which forms a predetermined angle to the axis of indication, said line segment having as its origin the point on the axis of indication where a position marking in simultaneously produced.

27. An apparatus as claimed in claim 15 comprising a holder for the sound angle probe and the ultrasonic apparatus, said ultrasonic apparatus having only an emission circuit and a receiving circuit for electric pulses to and from the sound probe and a control circuit for activating the indicating units, assembled into a single integrated battery-powered unit.

* * * * *

UNITED STATES PATENT OFFICE
CERTIFICATE OF CORRECTION

Patent No. 3,962,909            Dated June 15, 1976

Inventor(s) Svend Aage Lund

It is certified that error appears in the above-identified patent and that said Letters Patent are hereby corrected as shown below:

The spelling of the assignee is corrected to read as follows:

AKADEMIET FOR DE TEKNISKE VIDENSKABER, SVEJSECENTRALEN

Signed and Sealed this

Twenty-third Day of November 1976

[SEAL]

Attest:

RUTH C. MASON
*Attesting Officer*

C. MARSHALL DANN
*Commissioner of Patents and Trademarks*